(12) United States Patent
Miskie (10) Patent No.: US 7,361,803 B2
(45) Date of Patent: Apr. 22, 2008

(54) MULTI-LAYER MOISTURE MANAGEMENT FABRIC COMPOSITE

(76) Inventor: Mark Miskie, 815 Stargard Ct., Charlotte, NC (US) 28270

( * ) Notice: Subject to any disclaimer, the term of this patent is extended or adjusted under 35 U.S.C. 154(b) by 98 days.

(21) Appl. No.: 10/983,476

(22) Filed: Nov. 8, 2004

(65) Prior Publication Data
US 2006/0100597 A1 May 11, 2006

(51) Int. Cl.
A61F 13/537 (2006.01)
D03D 11/00 (2006.01)

(52) U.S. Cl. ................................................. 604/378
(58) Field of Classification Search .......... 604/385.12, 604/360, 358, 367, 380; 128/113.1; 428/36.2, 428/180, 190, 191; 442/205–207, 239, 79
See application file for complete search history.

(56) References Cited

U.S. PATENT DOCUMENTS

| | | | | |
|---|---|---|---|---|
| 2,896,618 A * | 7/1959 | Schaefer | ................... | 602/47 |
| 4,173,046 A * | 11/1979 | Gallagher | ................... | 5/484 |
| 4,338,371 A * | 7/1982 | Dawn et al. | ................. | 442/373 |
| 4,360,015 A * | 11/1982 | Mayer | ................... | 602/47 |
| 4,673,402 A * | 6/1987 | Weisman et al. | ........... | 604/368 |
| 5,334,176 A * | 8/1994 | Buenger et al. | ............ | 604/367 |
| 5,500,270 A * | 3/1996 | Langdon et al. | ............ | 428/131 |
| 5,614,283 A * | 3/1997 | Potnis et al. | ................. | 428/131 |
| 5,735,145 A * | 4/1998 | Pernick | ................... | 66/196 |
| 5,776,567 A * | 7/1998 | Schilling et al. | ........... | 428/34.5 |
| 5,833,678 A * | 11/1998 | Ashton et al. | .............. | 604/378 |
| 6,028,241 A * | 2/2000 | Armstead | ................... | 604/367 |
| 6,048,810 A * | 4/2000 | Baychar | ................... | 442/370 |
| 6,242,074 B1 * | 6/2001 | Thomas | ................... | 428/137 |
| 6,432,504 B1 * | 8/2002 | Yeh | ................... | 428/85 |
| 7,169,720 B2 * | 1/2007 | Etchells et al. | ............ | 442/239 |
| 2005/0148250 A1 * | 7/2005 | O'Connor et al. | ............ | 442/2 |

* cited by examiner

Primary Examiner—Tatyana Zalukaeva
Assistant Examiner—Laura C. Hill
(74) Attorney, Agent, or Firm—Schwartz Law Firm, P.C.

(57) ABSTRACT

A multi-layer moisture management fabric composite includes a three-dimensional fabric spacer. The spacer forms a first layer of the fabric composite. The spacer has a first facing adapted for residing nearest the skin, a second facing, and an intermediate spacer yarn interconnecting the first and second facings. A plurality of overlying moisture-absorbent layers reside outside of the spacer, and are adapted for receiving and dispersing moisture entering the fabric composite and passing through the first layer. A liquid impermeable jacket resides outside of the absorbent layers and defines an outermost layer of the fabric composite adapted for trapping liquid moisture within the absorbent layers.

20 Claims, 6 Drawing Sheets

MULTI-LAYER MOISTURE MANAGEMENT FABRIC COMPOSITE

TECHNICAL FIELD AND BACKGROUND OF THE INVENTION

This invention relates generally to a multi-layer moisture management fabric composite, and more specifically, to a moisture management incontinence pad designed for both men and women, and applicable for managing light, moderate and heavy urinary incontinence. The invention is especially useful for controlling multiple instances of leakage.

An estimated 19 million North American adults suffer urinary incontinence with severity ranging from partial to complete loss of bladder control. They may experience varying degrees of urine loss, and the incontinence may change over time. For example, some adults with light incontinence may leak a little when they laugh or cough, while others with heavy incontinence may be experience continuous leakage. No two cases are alike, and no two adults are affected by incontinence the same way.

Incontinence is not an inevitable part of aging, and it is not a disease. In fact, in most cases, it is merely a symptom or side-effect of another medical condition. Male urinary incontinence may be caused by any number of health conditions including prostate surgery, neurologic disease or injury (Parkinson's disease, stroke or spinal cord injury), obstructed urination, and certain birth defects or chronic medical conditions such as diabetes. In many cases, incontinence can be cured and it can always be managed. Many women will experience periods of urinary incontinence caused by childbirth and menopause.

Presently available commercial products address all levels of urinary incontinence. Prior art incontinence pads are generally either relatively inexpensive and disposable, or more expensive and reusable. The present invention focuses on the reusable pad market. Such pads typically include a moisture absorbing component combined with an overlying moisture barrier. The moisture barrier is designed to prevent movement of moisture through the moisture absorbing component and outwardly from the pad. When washing these pads for reuse, it is difficult to fully clean the moisture absorbing component due to the restricted flow of water through the pad caused by the moisture barrier. An even greater problem is the inability to efficiently and effectively dry the pad after washing. Thus, while an advantage of these pads lies in their repeated reusability, the considerable time and inconvenience in laundering generally outweighs the ultimate costs savings. Furthermore, when saturated, existing pads generally trap moisture directly against the skin of the user creating an uncomfortable and unhealthy environment prone to fungus and bacteria growth.

SUMMARY OF INVENTION

Therefore, it is an object of the invention to provide a moisture management incontinence pad which is launderable and reusable.

It is another object of the invention to provide a moisture management incontinence pad which can be efficiently and effectively cleaned.

It is another object of the invention to provide a moisture management incontinence pad which can be efficiently and effectively dried after washing.

It is another object of the invention to provide a moisture management incontinence pad which can be either used alone or in combination with a washable undergarment.

It is another object of the invention to provide a moisture management incontinence pad which promotes rapid osmotic pulling or wicking of moisture away from the skin of a user.

It is another object of the invention to provide a moisture management incontinence pad which utilizes a first wicking layer at a urine entry zone and then multiple layers of increasingly absorbent fabric.

It is another object of the invention to provide a moisture management incontinence pad which can be worn over an extended period of time.

It is another object of the invention to provide a moisture management incontinence pad which is specifically intended to receive and properly manage multiple instances of urine leakage without having to change the pad.

It is another object of the invention to provide a moisture management incontinence pad which is constructed such that all fabric layers including the outer barrier jacket are adjoined to ensure proper orientation when reconstructing the pad after laundering.

It is another object of the invention to provide a moisture management incontinence pad which incorporates a warp knit three-dimensional spacer fabric having a loft ranging from 1.5 mm to more than 15 mm.

It is another object of the invention to provide a moisture management incontinence pad which maximizes breathability, insulation, compression, recovery, and durability.

It is another object of the invention to provide a moisture management incontinence pad which incorporates a spacer fabric comprising two separate face fibers combined with an inner spacer yarn or yarns in a warp-knitted construction.

It is another object of the invention to provide a moisture management incontinence pad which incorporates a spacer fabric that can combine as many as three different fibers in any one desired construction, exploiting the particular properties of each fiber in the two facings and the spacer yarns between them.

It is another object of the invention to provide a moisture management incontinence pad which incorporates a spacer fabric constructed using all homogenous materials and no glues or laminates.

It is another object of the invention to provide a moisture management incontinence pad which incorporates a spacer that retains its qualities even after repeated washings.

It is another object of the invention to provide a moisture management incontinence pad which incorporates a spacer fabric that keeps the skin (which contacts the pad) dry, and prevents growth of fungus and bacteria.

It is another object of the invention to provide a moisture management incontinence pad which incorporates a spacer fabric that is relatively light.

These and other objects of the present invention are achieved in the preferred embodiments disclosed below by providing a multi-layer moisture management fabric composite. The fabric composite includes a three-dimensional fabric spacer which defines a first layer of the fabric composite. The spacer has a first facing adapted for residing nearest the skin, a second facing, and an intermediate spacer yarn interconnecting the first and second facings. A plurality of overlying moisture-absorbent layers reside outside of the spacer, and are adapted for receiving and dispersing moisture entering the fabric composite and passing through the first layer. A liquid impermeable jacket resides outside of the absorbent layers and defines an outermost layer of the fabric composite adapted for trapping liquid moisture within the absorbent layers.

According to another preferred embodiment, the fabric spacer has a loft greater than 0.06 inches.

According to another preferred embodiment, the first facing of the spacer is a fine mesh fabric.

According to another preferred embodiment, the fine mesh fabric has at least 400 uniform, mesh openings per square inch.

According to another preferred embodiment, the first facing of the spacer includes moisture wicking fibers adapted for promoting moisture flow by capillary wicking.

According to another preferred embodiment, the moisture wicking fibers are selected from a group consisting of polyester, nylon, and acrylic.

According to another preferred embodiment, the first facing of the spacer further includes antimicrobial fibers.

According to another preferred embodiment, the antimicrobial fibers include silver.

According to another preferred embodiment, the second facing of the spacer is an open mesh fabric.

According to another preferred embodiment, the open mesh fabric has less than 50 uniform, mesh openings per square inch.

According to another preferred embodiment, the second facing of the spacer includes moisture-absorbent fibers adapted for drawing moisture from the first facing of the spacer through the spacer yarn.

According to another preferred embodiment, the moisture-absorbent fibers are selected from a group consisting of cotton and wool.

According to another preferred embodiment, the intermediate spacer yarn of the spacer includes moisture wicking fibers adapted for promoting moisture flow from the first facing to the second facing by capillary wicking.

According to another preferred embodiment, the moisture wicking fibers are selected from a group consisting of polyester, nylon, and acrylic.

According to another preferred embodiment, a moisture wicking layer resides between the fabric spacer and the absorbent layers. The wicking layer includes wicking fibers adapted for promoting moisture flow by capillary wicking.

According to another preferred embodiment, the composite includes at least two overlying moisture-absorbent layers.

According to another preferred embodiment, the absorbent layers include hydrophillic fibers selected from a group consisting of cotton, felt, and wool.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
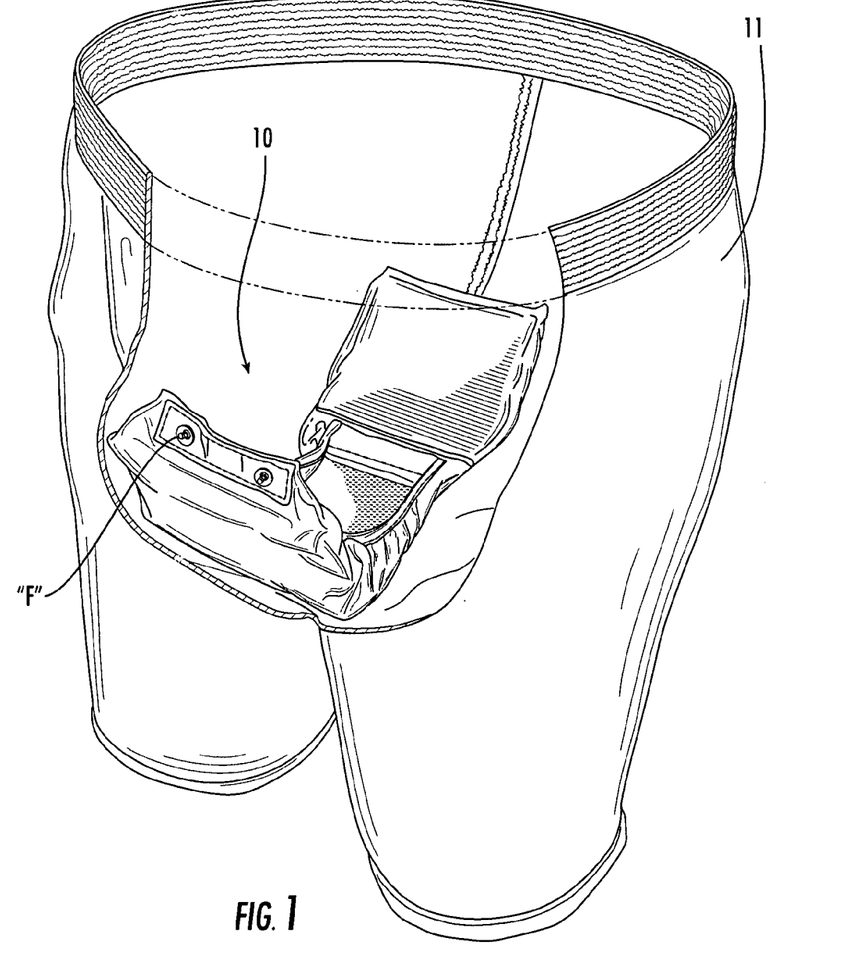
FIG. 1 is an environmental perspective view of a moisture management incontinence pad according to one preferred embodiment of the present invention, and showing the pad incorporated inside an undergarment.

Referring now specifically to the drawings, a moisture management incontinence pad according to the present invention is illustrated in FIG. 1, and shown generally at reference numeral 10. The incontinence pad 10 is designed for both men and women, and is especially useful for wear at night to manage multiple instances of moderate to heavy urine leakage while sleeping. The incontinence pad 10 is adapted for suspension inside an undergarment 11 using any suitable fastener "F", such as snaps, hook and loop fasteners, or the like. The undergarment 11 resembles a conventional sport brief including an elastic waistline, a front and rear joined to the waistline, and first and second leg segments defining respective leg openings. The undergarment 11 has complementary fasteners (not shown) designed to mate with the fasteners "F" of the incontinence pad 10 to position and retain the pad 10 inside the undergarment 11.

Figure 2:
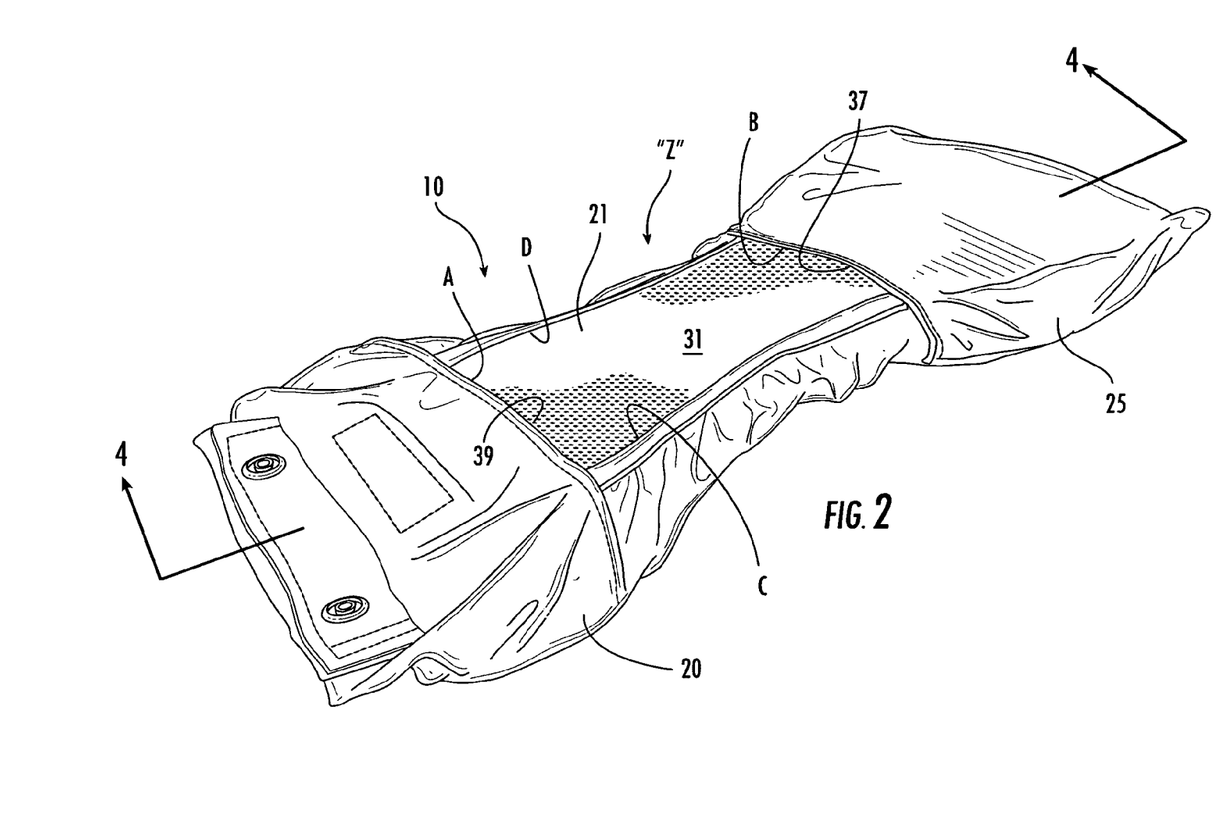
FIG. 2 is a perspective view of the incontinence pad.
Figure 3:
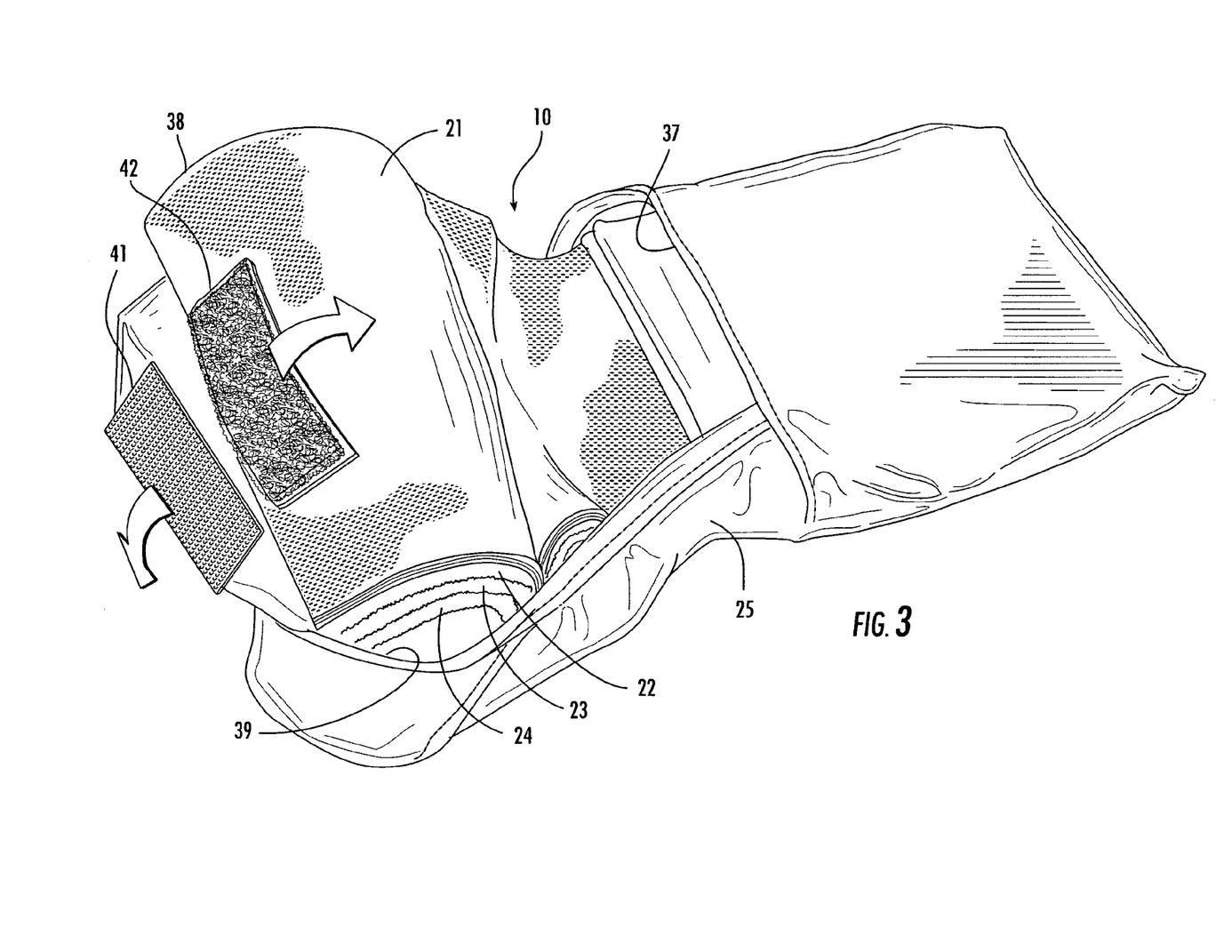
FIG. 3 is a further perspective view of the incontinence pad demonstrating the process for turning the pad inside out for laundering.
Figure 4:
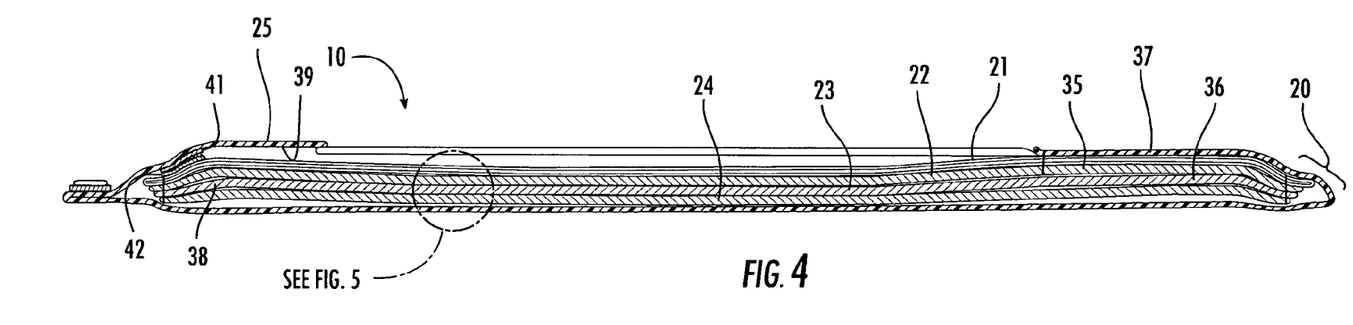
FIG. 4 is a cross-sectional view of the incontinence pad taken substantially along line 4-4 of FIG. 2.

As best shown in FIGS. 2, 3 and 4, the incontinence pad 10 is constructed of a multi-layer moisture management fabric composite 20. The fabric composite 20 comprises a three-dimensional fabric spacer 21, a wicking layer 22, and a number of moisture-absorbent layers 23 and 24—all substantially encased within a non-porous, fluid impermeable, moisture vapor permeable jacket 25. The fabric composite 20 has an inside major surface which resides nearest the body of the user, and an outside major surface which resides nearest the undergarment 11.

Figure 8:
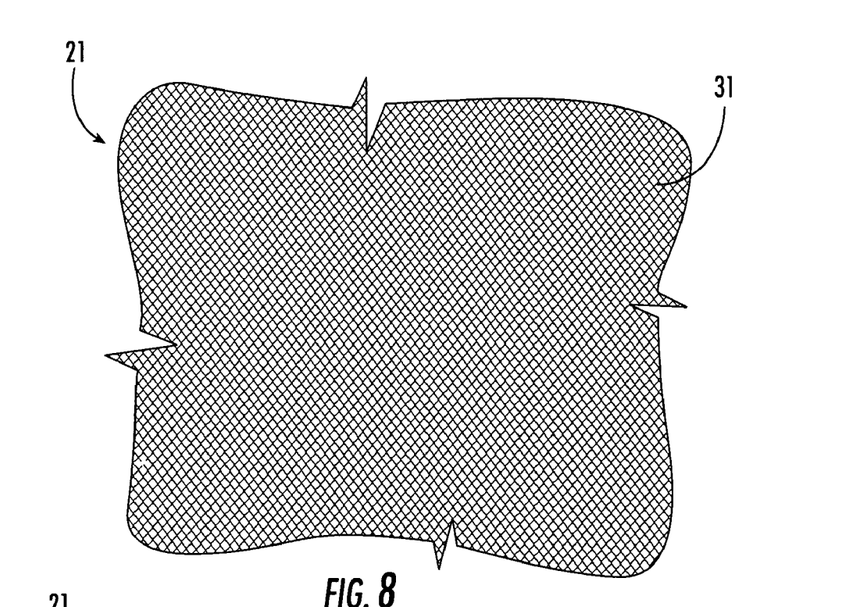
FIG. 8 is an enlarged plan view showing the fine mesh side of the fabric spacer.

The 3-dimensional fabric spacer 21 comprises an inner layer of the composite 20, and consists of two independently constructed fabric facings 31 and 32 integrally formed with a system of intermediate spacer yarns 33. Examples of this construction are described in U.S. Pat. Nos. 6,103,641 and 6,627,562 incorporated herein by reference. The spacer 21 is produced on a two needle bar Raschel machine, and has a loft ranging from 0.06 inches to more than 0.6 inches. According to one embodiment, the loft is approximately 0.1875 inches. The loft is preferably greater than 25% of the total composite thickness. The first facing 31 which resides nearest the skin of the user comprises a relatively fine mesh fabric (See FIG. 8) consisting substantially of low moisture-absorbent fibers, such as acrylic, or non-absorbent hydrophobic fibers, such as polypropylene. These fibers resist swelling and compression when wet, and promote the rapid transport of moisture away from the inner layer of the fabric composite 20 and the skin of the user. The quantity of low and/or non-absorbent fibers is greater than 50% of the total fiber incorporated in the facing 31, and more preferably, between 85% and 100%. A "low absorbent" fiber is defined as one with less than 10% swell when wet. A "non-absorbent" fiber has less than 5% swell when wet. Preferably, the mesh fabric has at least 400 uniform, generally round, mesh openings per square inch. To deter the growth of fungus and bacteria, the first facing 31 may also include antimicrobial fibers comprising silver. Suitable antimicrobial fibers are disclosed in prior U.S. Pat. No. 6,723,428 incorporated herein by reference.

The spacer yarns 33 comprise moisture-wicking fibers, such as acrylic and polyester, which are made to promote the transport of moisture by capillary wicking. Examples of commercially available wicking fibers include Isolfil® by Di Borio Fiorino, Dacron® by E. I. du Pont de Nemours and Company, and Coolmax® by Invista. The mechanical structure and compressibility of the fiber determine its overall wicking potential. CoolMax® fibers, for example, have four longitudinal channels built into their cross-sectional geometry giving a 20% higher perimeter area than traditional round fibers. The result is higher water/vapor transport through enhanced surface exposure for capillary action. Capillary action attracts water from the first facing 31 of the spacer 21 where it is abundant and rapidly transports it to the second facing 32 of the spacer 21 where it is less abundant. Preferably, the spacer yarns 33 consist of between 85% and 100% wicking fibers.

Figure 9:
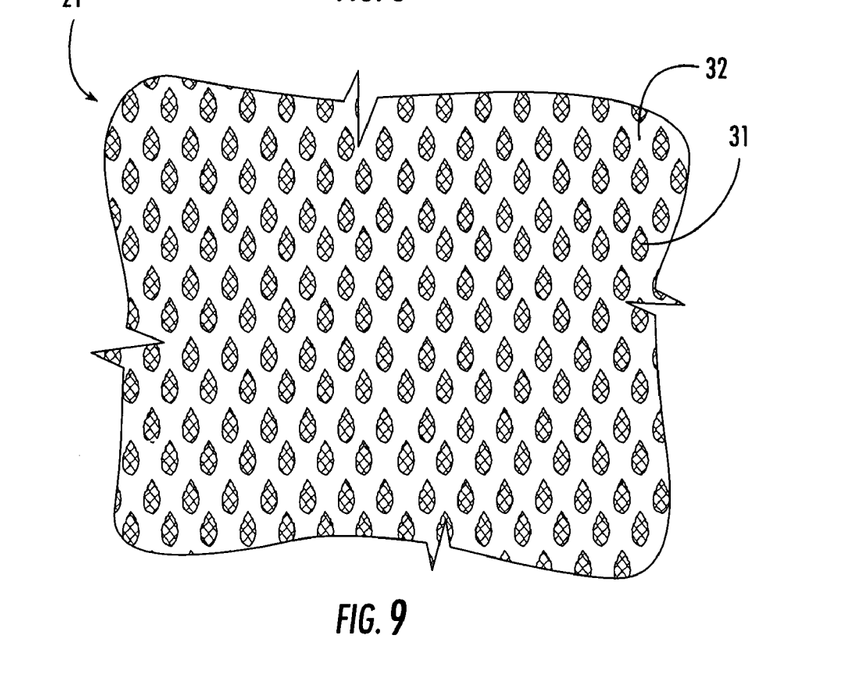
FIG. 9 is an enlarged plan view showing the open mesh side of the fabric spacer.

The second fabric facing 32 adjacent the spacer yarns 33 is constructed of high moisture-absorbent fibers, such as cotton and wool, and/or wicking fibers, such as polyester and acrylic, which operate to draw moisture inwardly from the first facing 31 and spacer yarns 33, and disperse it over the entire surface area of the outside facing 32. The second facing 32 comprises a highly breathable, open mesh fabric (See FIG. 9) which promotes air circulation within and through the spacer 21. Preferably, the mesh fabric has less than 50 uniform, generally oval, mesh openings per square inch. A "high" moisture-absorbent fiber is defined herein as one which swells in excess of 20% when wet.

The wicking layer 22 resides adjacent the fabric spacer 21, and cooperates with the overlying moisture-absorbent layers 23 and 24 to further move moisture outwardly away from the skin of the user. The wicking layer 22 engages the wet fibers of the spacer 21, and through capillary action further transports moisture to the outer, highly absorbent layers 23, 24 where the moisture is further dispersed. The wicking layer 22 consists substantially of wicking fibers such as polyester and acrylic. The moisture-absorbent layers 23, 24 comprise cotton, wool, and felt which swell up to 45% when wet.

The liquid impermeable, vapor permeable jacket 25 resides adjacent the outermost absorbent layer 24, and covers the end edges and opposing side edges of the overlying composite layers 21-24. The sides of the jacket 25 comprise elastic yarns, such as Spandex®, which give the incontinence pad 10 a generally cupped shape for improved fit and added comfort. The jacket 25 serves to trap liquid within the fabric composite 20, and forms a breathable vapor-permeable moisture barrier between the composite 20 and the undergarment 11.

Urine enters the incontinence pad 10 through a moisture entry zone "Z" which communicates with an entirely exposed portion of the inside major surface of the fabric composite 20. As shown in FIG. 2, the moisture entry zone "Z" is defined by an area of the fabric composite 20 extending between points A, B, C, and D of the jacket 25. Preferably, the jacket 25 wraps around the ends and sides of the fabric composite 20 covering greater than 20 percent of the inside major surface, thereby reducing the likelihood of urine leakage outwardly from the incontinence pad 10 and onto the undergarment 11 and bed sheets. In this embodiment, the moisture entry zone "Z" comprises less than 80 percent of the inside major surface of the fabric composite 20. During each incidence of leakage, urine is received through the entry zone "Z" and immediately passed into the fabric composite 20 for transport away from the body.

Figure 5:
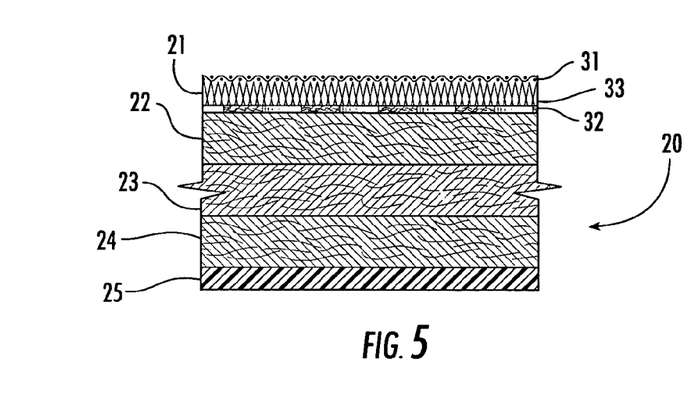
FIG. 5 is an enlarged, fragmentary, cross-sectional view of the area indicated in FIG. 4.

As shown in FIGS. 4 and 5, the spacer 21, wicking layer 22, and absorbent layers 23, 24 of the fabric composite 20 reside in overlying registration and are sewn together at respective opposite ends. In addition, the spacer 21 and wicking layer 22 are sewn together and to the jacket 25 at an intermediate point 35. For more effective and efficient laundering, the opposing sides of all layers 21-24 remain substantially unattached in order to promote air and water circulation through the fabric composite 20 between adjacent layers. The term "substantially unattached" as used herein means unattached along more than 50% of the entire length of a single side edge or end edge, and preferably more than 80% of the entire length of the side edge or end edge. The term "laundering" is broadly defined herein to mean any step in the cleaning process including washing and air drying.

The fixed end 36 of the composite layers 21-24 resides within a lateral end pocket 37 of the jacket 25 and is permanently secured to the jacket 25 at point 35, as previously described. The free end 38 of the composite layers 21-24 is received inside a second lateral end pocket 39 of the jacket 25. As shown in FIG. 3, the free end 38 is releasably secured to the jacket 25 by complementary patches of hook and loop fasteners 41 and 42. Prior to washing and drying the incontinence pad 10, the free end 38 of the attached composite layers 21-24 is removed from the end pocket 39 and extended away from the jacket 25. The attached fabric layers 21-24 are open along respective opposite sides to allow effective cleaning of the interior layers, and to promote fast and efficient drying. After laundering, the composite layers 21-24 are replaced inside the end pocket 39 of the jacket 25, and the complementary hook and loop fasteners 41, 42 reattached.

Figures 6, 7:
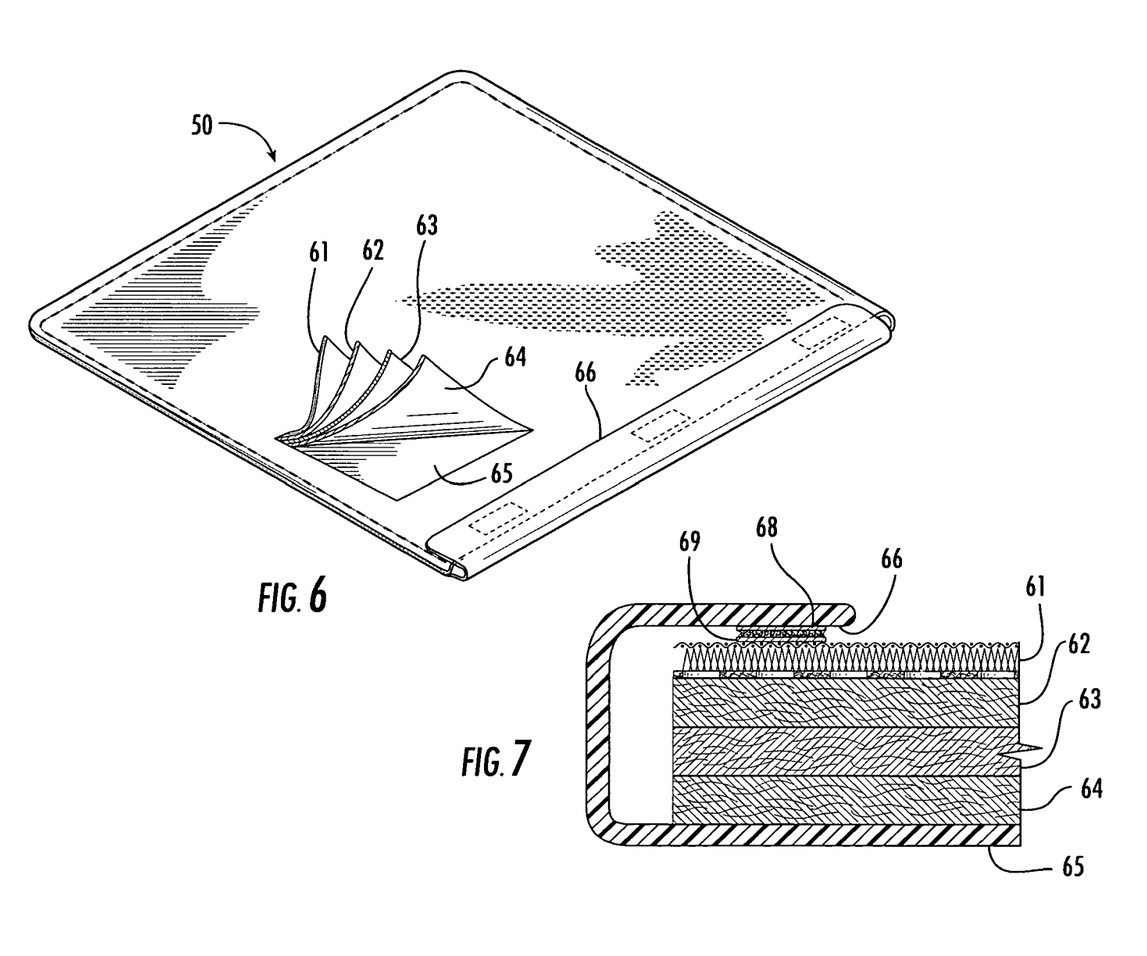
FIG. 6 is a perspective view of a moisture management bed pad which incorporates the present fabric composite.
FIG. 7 is an enlarged, fragmentary, cross-sectional view of the bed pad.

According to a further embodiment, shown in FIGS. 6 and 7, the present fabric composite is incorporated in a moisture management bed pad 50. As previously described, the fabric composite 60 comprises a three-dimensional fabric spacer 61, a wicking layer 62, a number of moisture-absorbent layers 63, 64, and a non-porous, fluid impermeable, moisture vapor permeable jacket 65. The fabric composite 60 has an inside major surface which is intended to reside nearest the body of the user, and an outside major surface. The jacket 65 serves as a moisture barrier for trapping moisture inside the fabric composite 60 without outward leakage.

Preferably, the overlying composite layers 61-64 are attached to the jacket 65 by sewing, and are substantially unattached to each other along at least one common side edge. A pocket 66 formed by the jacket 65 and extending along a margin of the bed pad 50 allows the pad 50 to be turned inside out for more effective and efficient laundering. The other three side edges of the jacket 65 are sewn directly and continuously along respective joined edges of the composite layers 61-64. Complementary patches of hook and loop fasteners 68 and 69 serve to releasable close the pocket 66 during use.

A multi-layer moisture management fabric composite is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A multi-layer moisture management fabric composite, comprising:
    (a) a three-dimensional integrally formed fabric spacer forming a first layer of said fabric composite, and having a first facing comprising a relatively smaller mesh fabric adapted for residing nearest the skin, a second facing comprising a relatively larger mesh fabric, and an intermediate spacer yarn layer interconnecting the first and second facings;
    (b) a plurality of overlying moisture-absorbent layers comprising hydrophilic fibers residing outside of said spacer, and adapted for receiving and dispersing moisture entering said fabric composite and passing through said first layer, whereby said hydrophilic fibers reside against the open mesh fabric of said second facing and promote rapid transfer of moisture through said first layer and into said overlying moisture-absorbent layers; and
    (c) a liquid impermeable jacket residing outside of said absorbent layers and defining an outermost layer of said fabric composite adapted for trapping liquid moisture within said absorbent layers.

2. A moisture management fabric composite according to claim 1, wherein said fabric spacer has a loft greater than 0.06 inches.

3. A moisture management fabric composite according to claim 1, wherein the first facing of said spacer comprises a smaller mesh fabric having at least 8 times the number of mesh openings as the second facing of said spacer.

4. A moisture management fabric composite according to claim 3, wherein said smaller mesh fabric comprises at least 400 uniform, mesh openings per square inch.

5. A moisture management fabric composite according to claim 1, wherein the first facing of said spacer comprises moisture wicking fibers adapted for promoting moisture flow by capillary wicking.

6. A moisture management fabric composite according to claim 5, wherein said moisture wicking fibers are selected from a group consisting of polyester, nylon, and acrylic.

7. A moisture management fabric composite according to claim 5, wherein the first facing of said spacer further comprises antimicrobial fibers.

8. A moisture management fabric composite according to claim 7, wherein said antimicrobial fibers comprise silver.

9. A moisture management fabric composite according to claim 1, wherein the second facing of said spacer comprises a larger mesh fabric having less than an eighth of the number of mesh openings as the first facing of said spacer.

10. A moisture management fabric composite according to claim 9, wherein said large mesh fabric comprises less than 50 uniform, mesh openings per square inch.

11. A moisture management fabric composite according to claim 1, wherein the second facing of said spacer comprises moisture-absorbent fibers adapted for drawing moisture from the first facing of said spacer through said spacer yarn.

12. A moisture management fabric composite according to claim 11, wherein said moisture-absorbent fibers are selected from a group consisting of cotton and wool.

13. A moisture management fabric composite according to claim 1, wherein the intermediate spacer yarn of said spacer comprises moisture wicking fibers adapted for promoting moisture flow from the first facing to the second facing by capillary wicking.

14. A moisture management fabric composite according to claim 13, wherein said moisture wicking fibers are selected from a group consisting of polyester, nylon, and acrylic.

15. A moisture management fabric composite according to claim 1, and comprising a moisture wicking layer residing between said fabric spacer and said absorbent layers, said wicking layer comprising wicking fibers adapted for promoting moisture flow by capillary wicking.

16. A moisture management composite fabric according to claim 1, and comprising at least two overlying moisture-absorbent layers.

17. A moisture management fabric composite according to claim 1, wherein said absorbent layers comprise hydrophillic fibers selected from a group consisting of cotton, felt, and wool.

18. A multi-layer moisture management fabric composite, comprising:
    (a) a three-dimensional, integrally-knit fabric spacer forming a first layer of said fabric composite, and having a loft greater than 0.06 inches; said a three-dimensional fabric spacer having a first facing comprising a relatively smaller mesh fabric adapted for residing nearest the skin, a second facing comprising a relatively larger mesh fabric, and an intermediate spacer yarn layer interconnecting the first and second facings;
    (b) a plurality of overlying moisture-absorbent layers comprising hydrophilic fibers residing outside of said spacer, and adapted for receiving and dispersing moisture entering said fabric composite and passing through said first layer, whereby said hydrophilic fibers reside against the larger mesh fabric of said second facing and promote rapid transfer of moisture through said first layer and into said overlying moisture-absorbent layers; and
    (c) a liquid impermeable jacket residing outside of said absorbent layers and defining an outermost layer of said fabric composite adapted for trapping liquid moisture within said absorbent layers.

19. A moisture management fabric composite according to claim 18, wherein said spacer defines an inside facing comprising a smaller mesh fabric having at least 400 uniform, mesh openings per square inch.

20. A moisture management fabric composite according to claim 19, wherein said spacer defines an outside facing comprising a larger mesh fabric having less than 50 uniform, mesh openings per square inch.

* * * * *